US007985831B2

(12) United States Patent
Niwa et al.

(10) Patent No.: US 7,985,831 B2
(45) Date of Patent: Jul. 26, 2011

(54) CROHN'S DISEASE ANTIBODY EPITOPE PEPTIDE AND REAGENT FOR TESTING CROHN'S DISEASE

(75) Inventors: Mikio Niwa, Tsukuba (JP); Katsuhiko Matsuo, Tsukuba (JP); Keiichi Mitsuyama, Kurume (JP); Michio Sata, Fukuoka (JP)

(73) Assignees: Toagosei Co., Ltd., Tokyo (JP); Kurume University, Fukuoka (JP)

( * ) Notice: Subject to any disclaimer, the term of this patent is extended or adjusted under 35 U.S.C. 154(b) by 1204 days.

(21) Appl. No.: 11/659,345

(22) PCT Filed: Apr. 26, 2005

(86) PCT No.: PCT/JP2005/007857
§ 371 (c)(1),
(2), (4) Date: Feb. 5, 2007

(87) PCT Pub. No.: WO2006/013661
PCT Pub. Date: Feb. 9, 2006

(65) Prior Publication Data
US 2009/0170115 A1    Jul. 2, 2009

(30) Foreign Application Priority Data

Aug. 5, 2004  (JP) ................. 2004-229171

(51) Int. Cl.
*A61K 38/00* (2006.01)
*A61K 39/00* (2006.01)
*A61K 38/04* (2006.01)
(52) U.S. Cl. ............ 530/300; 424/184.1; 530/328
(58) Field of Classification Search .......... None
See application file for complete search history.

(56) References Cited

FOREIGN PATENT DOCUMENTS

| EP | 1 391 462 A1 | 2/2004 |
| WO | WO 01/57182 A2 * | 9/2001 |
| WO | WO 01/64835 A2 * | 9/2001 |
| WO | WO 02/088175 | 11/2002 |

OTHER PUBLICATIONS

Greenspan et al. (Nature Biotechnology 7: 936-937, 1999).*
Bowie et al (Science, 1990, 257:1306-1310).*
Saito, H., et al., "Isolation of peptides useful for differential diagnosis of Crohn's disease and ulcerative colitis", Gut, 2003; 52; 535-540.
Mow, William S., et al., "Association of Antibody Responses to Microbial Antigens and Complications of Small Bowel Crohn's Disease", Gastroenterology, 2004, 126: 414-424.
Vermeire et al., "Antibody responses in Crohn's disease", Gastroenterology Vol. 126, No. 2, pp. 691-604, Feb. 2004.
Peeters, March, M.D., et al., "Diagnostic Value of anti-*Saccharomyces cerevisiae* and Antineutrophil cytoplasmic Autoantibodies in Inflammatory Bowel Disease", The American Journal of Gastroenterology, vol. 96, No. 3, 2001 pp. 730-734.
Naser, S., et al., "Specific seroreactivity of Crohn's disease patients against p35 and p 36 antigens of *M. avium* subsp. *paratuberculosis*", Veterinary Microbiology, 77 (2000), pp. 497-504.

* cited by examiner

*Primary Examiner* — Vanessa L. Ford
(74) *Attorney, Agent, or Firm* — Fitch, Even, Tabin & Flannery

(57) ABSTRACT

An epitope peptide is provided, which is capable of binding specifically to an antibody characteristic of Crohn's disease that is specifically observed in patients with Crohn's disease, together with a test method for conveniently and rapidly determining whether a subject is affected by Crohn's disease by use of the above peptide. The epitope peptide to the Crohn's disease antibody comprises a peptide having an amino acid sequences represented by any one of SEQ ID NOS: 1 to 3 or a salt thereof. A test reagent and a test method for Crohn's disease are provided, which comprise the peptide as an active ingredient.

4 Claims, 9 Drawing Sheets

Fig. 8

| Homology search result - TCP-47 - | | | |
|---|---|---|---|
| N-terminal | Homologous sequence | C-terminal | |
| 6 | EVEEVTFTK<br>\|\|:\|\|\|\|\|\|\| | 14 | TCP-47 (27 a.a.) |
| 14988 | EVDEVTFTK | 14996 | D-Titin (16215 a.a.) [Drosophila melanogaster] |
| 7 | VE---EVTPTKHTQCLGCFKSGF<br>\|\|  \|\|\|        \|\|\|\|\|\| \| | 26 | TCP-47 (27 a.a.) |
| 308 | VERKREVT-------LGCFKSDF | 323 | DNA methyltransferase Dim-2 (1454 a.a.)<br>[Neurospora crassa] |
| 6 | EVEEVTFTKHT<br>:\|:\|\|  \|:\|\|\| | 16 | TCP-47 (27 a.a.) |
| 1880 | DVDEVAFSKHT | 1890 | Viral protein (2292 a.a.) [Encephalomyocarditis virus] |
| 1 | NSVKNEVEEVT<br>\|\|\|\|\|:\|:\| \| | 11 | TCP-47 (27 a.a.) |
| 55 | NSVKNDVDEST | 65 | Hypothetical protein (168 a.a.) [Dictyosterium discoideum] |
| 1 | NSVKNEVEEVTFTKH-TQ<br>::\|\| \|\|\|\|\|   \|\| \|\| | 17 | TCP-47 (27 a.a.) |
| 215 | DNVKIEVEEV-INKHITQ | 231 | Hypothetical protein (249 a.a.) [Trichodesmium erythraeum] |
| 1 | NSVKNEVEEVTFTKHTQ<br>\|:\|\| \|\|\|\|    \|\|:: | 17 | TCP-47 (27 a.a.) |
| 1574 | NNVKEEVEE----KHSE | 1586 | Hypothetical protein (3724 a.a.) [Plasmodium falciparum] |
| 7 | VE-EVTFTK-------HTQC<br>\|\| :\|\|\|\|\|      \|:\|\| | 18 | TCP-47 (27 a.a.) |
| 140 | VECDVTFTKDRQKVCRHSQC | 159 | Glycerophosphoryl diester phosphodiesterase (458 a.a.)<br>[Rhodospirillum rubrum] |
| 1 | NSVKNEVEEVTFTKHTQCLG<br>\|\|\|\|:\|\|:\|  \|\|    \|\| | 20 | TCP-47 (27 a.a.) |
| 64 | NSVKDEVKE--FTNQ---LG | 78 | Hypothetical protein (417 a.a.) [Pyrococcus horikoshii] |
| 6 | EVEEVTF<br>\|\|\|\|\|\|\| | 12 | TCP-47 (27 a.a.) |
| 4939 | EVEEVTF | 4945 | Novex-3 Titin Isoform (5604 a.a.) [Homo sapiens] |

Fig. 9

| Homology search result - TCP-336 - | | | |
|---|---|---|---|
| N-terminal | Homologous sequence | C-terminal | |
| 1 | VIPALSEAEAGGSPEVRSSRPAWP<br>\|\|\|\|\| \|\|\| \|\|\|\|\|\|\|\|\|\|\|\|\|\| | 24 | TCP-336 (26 a.a.) |
| 80 | VIPALWEAEVGGSPEVRSSRPAWP | 103 | unnamed protein (124 a.a.) [Homo sapiens] |
| 1 | VIPALSEAEAGGSPEVRSSRPAWPIW<br>\|\|\|\|\| \|\|\|\|\| \|\|\|\|\|\| \|\|\|\|\| \| | 26 | TCP-336 (26 a.a.) |
| 293 | VIPALWEAEAGESPEVRSLRPAWPTW | 318 | cAMP responsive element binding protein-like 1 (318 a.a.)<br>[Homo sapiens] |
| 1 | VIPALSEAEAGGSPEVRSSRPAWPIW<br>\|\|\|\|\| :\|\|\|\|\| \|\|:\|\|\|\|\|\|\|\|  \| | 26 | TCP-336 (26 a.a.) |
| 74 | VIPALWKAEAGGLPELRSSRPAWTTW | 99 | MOST-1 protein (99 a.a.) [Homo sapiens] |

Fig. 10

| Homology search result - TCP-353 - ||||
|---|---|---|---|
| N-terminal | Homologous sequence | C-terminal | |
| 2 | IRGLFPN | 8 | TCP-353 (8 a.a.) |
|  | ┃┃┃┃┃┃┃ |  |  |
| 763 | IRGLFPN | 769 | putative chloride channel protein (773 a.a.) [Oryza sativa] |
| 1 | MIRGLF----PN | 8 | TCP-353 (8 a.a.) |
|  | ┃┃┃┃┃┃    ┃┃ |  |  |
| 98 | MIRGLFFVIHPN | 109 | Translation EF-P/translation eIF-5A (301 a.a.) [Azotobacter vinelandii] |
| 1 | MIRGLFP | 7 | TCP-353 (8 a.a.) |
|  | :┃┃┃┃┃┃ |  |  |
| 16 | LIRGLPP | 22 | retrotransposon gag protein and Zn-finger (915 a.a.) [Caenorhabditis elegans] |
| 1 | MIRGLPPN | 8 | TCP-353 (8 a.a.) |
|  | :┃┃ ┃┃┃┃ |  |  |
| 95 | LIRSLFPN | 102 | possible dynein heavy chain alpha (2613 a.a.) [Leishmania major] |

CROHN'S DISEASE ANTIBODY EPITOPE PEPTIDE AND REAGENT FOR TESTING CROHN'S DISEASE

This Application is the National Phase of International Application No. PCT/JP2005/007857 filed Apr. 26, 2005, which designated the U.S. and was not published under PCT Article 21(2) in English, and this application claims, via the aforesaid International Application, the foreign priority benefit of and claims the priority from Japanese Application No. 2004-229171, filed Aug. 5, 2004, the complete disclosures of said International Application and said Japanese Application, including any and all sequence listings, are incorporated herein by reference.

TECHNICAL FIELD

The present invention relates to a peptide useful for diagnosis of Crohn's disease, and to a test reagent containing the same as an active ingredient. The test reagent can be used for a Crohn's disease test method that can be carried out conveniently and rapidly by means of an immunological process using a biological specimen such as blood.

BACKGROUND OF ART

Crohn's disease, the cause of which is not known, is called inflammatory bowel disease which includes ulcerative colitis as well. When abdominal pain, diarrhea, weight loss, fever and the like are seen continually in young individuals (in their late 10s to early 20s), this disease should be suspected. Diagnosis is based on a combination of clinical symptoms, radiography, and endoscopy or pathological examination, etc. However, these techniques require experience and expertise, and hence diagnosis may be difficult in some cases. In particular, in an early stage of the disease, it is difficult to distinguish Crohn's disease from ulcerative colitis in many cases. On the other hand, gastrointestinal radiography and endoscopy, which are the principal diagnostic techniques, are disadvantageous in that they are painful to patients physically or psychologically. Accordingly, a reagent and a method for diagnosing Crohn's disease in vitro in a convenient and accurate manner are desired.

With regard to etiology of inflammatory bowel disease, it has long been reported that exogenous factors such as bacteria, viruses and alimentary antigens are related to intestinal inflammation. As for Crohn's disease in particular, there have been reported cases of infection and detection of *Mycobacterium paratuberculosis* (Non-patent documents 1 to 4, etc.); cases of detection of antibodies to baker's yeast and neutrophil (Non-patent documents 5 and 6, etc.), and cases of detection of an antibody to swine amylase or detection of an antibody to a Crohn's disease antibody binding peptide (see Patent documents 1 and 2). Some of these also reported antibodies specific to the disease, but none of them by itself showed a sufficient positive percentage for patients with Crohn's disease, posing a problem of a high false positive rate for ulcerative colitis which must be discerned therefrom. Under these circumstances, it is extremely important to develop a clinical test method by which Crohn's disease can be specifically diagnosed in a convenient and rapid manner at a high accuracy utilizing an antigen peptide specific to Crohn's disease.

Patent document 1: Japanese Patent Laid-Open (Kokai) No. H11-190734 (Claims)
Patent document 2: International publication WO 02/088175 (Disclosure of the Invention)

Non-patent document 1: Elsaghier A, et al. Clin Exp Immunol., 1992, 90, 503-508
Non-patent document 2: El-Zaatari F. A. et al. Curr Microbiol., 1999, 39, 115-119
Non-patent document 3: Naser S, et al. Vet Microbiol., 2000, 77, 497-504
Non-patent document 4: Suenaga K, et al. Dig Dis Sci., 1999, 44, 1202-1207
Non-patent document 5: Quinton J F, et al. Gut, 1998, 42, 788-791
Non-patent document 6: Peeters M, et al. Am J. Gastroenterol., 2001, 96, 730-734

DISCLOSURE OF THE INVENTION

Problems to be Solved by the Invention

Under the circumstances described above, the object of the present invention is to provide an epitope peptide specifically binding to an antibody which is specifically observed in patients with Crohn's disease and thus characteristic of Crohn's disease; a test reagent and a test kit containing the peptide as an active ingredient; and a test method of conveniently and rapidly examining whether or not patients are affected by Crohn's disease, by use of these.

Means for Solving the Problems

In order to solve the problems described above, the present inventors have conducted immunological and molecular biological studies, and have discovered that certain peptides specifically recognize and bind to specific antibodies that are present in sera of Crohn's disease patients. It has been confirmed that whether patients are affected by Crohn's disease can be determined conveniently and accurately by use of these peptides. Accordingly, the present invention is defined by the following (1) to (4):

(1) A peptide characteristic of an epitope to a Crohn's disease antibody, which is represented by the following (a) or (b):
  (a) a peptide comprising an amino acid sequence represented by any one of SEQ ID NOS: 1 to 3, or a salt thereof; and
  (b) a peptide comprising a modified amino acid sequence of any one of SEQ ID NOS: 1 to 3 in which one or some of the amino acids are substituted, deleted or added, and having a property of binding to an antibody in a Crohn's disease patient serum, or a salt thereof.
(2) A test reagent for Crohn's disease, comprising, as an active ingredient, the above peptide (a) or (b) characteristic of an epitope to a Crohn's disease antibody.
(3) A test kit for Crohn's disease, comprising the above test reagent for Crohn's disease as an antigen substance to a Crohn's disease antibody.
(4) A test method for Crohn's disease, comprising a step of determining whether an antibody that binds to the above peptide (a) or (b) is present or not in a biological specimen.

Hereinafter, abbreviations of amino acids, peptides, base sequences, etc., are indicated in this specification in accordance with the rules of IUPAC and IUB, "the Guideline for preparing specifications, etc., containing base sequences or amino acid sequences" (edited by Japan Patent Office), and the conventional symbols used in the art.

Further, a Crohn's disease antibody herein refers to an antibody which is generated in a living body suffering from Crohn's disease and thus characteristic of Crohn's disease as described above, and therefore means an antibody which is observed specifically in Crohn's disease patients regardless of types of causative antigens and thus characteristic of Crohn's disease.

Effects of the Invention

In accordance with the present invention, a Crohn's disease antibody epitope peptide specifically binding to a Crohn's disease antibody that is observed specifically in patients with Crohn's disease is provided, and included in a test reagent or a test kit for diagnosis of Crohn's disease. Thus, a useful testing method for Crohn's disease is also provided, which can examine and determine whether a patient is affected by Crohn's disease, in a convenient, rapid and accurate manner.

BEST MODE FOR CARRYING OUT THE INVENTION

1. Epitope Peptides to Crohn's Disease Antibody

The epitope peptide to the Crohn's disease antibody according to the present invention can be specifically exemplified by a peptide having an amino acid sequence represented by any one of SEQ ID NOS: 1 to 3.

In addition to the peptide having an amino acid sequence represented by any of SEQ ID NOS: 1 to 3, the epitope peptide to the Crohn's disease antibody according to the present invention may be a peptide having an amino acid sequence of any one of SEQ ID NOS: 1 to 3 wherein one or some (two or more) of the amino acids are substituted or supplemented with another amino acid or deleted. Thus, the epitope peptide to the Crohn's disease antibody according to the present invention encompasses the peptide having an amino acid sequence which is modified with the substitution, deletion or addition of one or more amino acids in each of these amino acid sequences, or having a part of such amino acid sequences, as long as the peptide has a property of specifically binding to the Crohn's disease antibody.

All the peptides described above are characterized by specifically binding to the Crohn's disease antibody.

There is no particular restriction to be placed on degree, site or the like of the substitution, deletion or addition of amino acids, as long as the modified peptide is characterized by specifically binding to the Crohn's disease antibody comparably to the peptide having an amino acid sequence represented by any one of SEQ ID NOS: 1 to 3.

Although modification (mutagenesis) of amino acid sequences occurs due to mutation, post-translational modification or the like, it can be induced artificially. Methods for modification (mutagenesis) of amino acid sequences are techniques well-known in the art, including genetic engineering techniques such as site-specific mutagenesis (Methods in Enzymology, 154, 350, 367-382 (1987); Ditto, 100, 468 (1983); Nucleic Acids Res., 12, 9441 (1984); Zoku Seikagaku Jikken Koza 1 "Idenshi Kenkyuho II" in Japanese transliteration that means Sequel Biochemical Experiment Lecture 1, "Gene Study Methodology II", as well as chemical synthesis techniques such as the phosphotriester method and the phosphoramidite method (J. Am. Chem. Soc., 89, 4801 (1967); Ditto, 91, 3350 (1969); Science, 150, 178 (1968); Tetrahedoron Lett., 22, 1859 (1981); Ditto, 24, 245 (1983)).

Further, in the epitope peptides of the Crohn's disease antibody according to the present invention exemplified by the peptides of the amino acid sequences represented by SEQ ID NO: 1, SEQ ID NO: 2, and SEQ ID NO: 3, the C-terminal may be any of carboxyl group (—COOH), amide group (—CONH$_2$), and ester group (—COOR). Here, R in the ester group includes, for example, $C_{1-6}$ alkyl groups such as methyl, ethyl, n-propyl, isopropyl and n-butyl; $C_{3-8}$ cycloalkyl groups such as cyclopentyl and cyclohexyl; and $C_{6-12}$ aryl groups such as phenyl and α-naphthyl.

When a peptide used in the present invention has a carboxyl group at a site other than the C-terminal, such a carboxyl group may be amidized or esterified, and such a peptide is also included in the peptide of the present invention. Such esters in this instance include, for example, those described above for the C-terminal esters.

Further, the peptides of the present invention also include those in which an amino acid group of the amino acid residue at the N-terminal is protected by a protecting group (for example, $C_{1-6}$ acyl group such as formyl group and acetyl group); those in which a glutamine residue at the N-terminal generated by cleavage in the living body is changed to pyroglutamic acid; those in which a substituent (for example, hydroxyl group, mercapto group, amino group, imidazole group, indole group, and guanidino group) on a side chain of an amino acid in the molecule is protected by a suitable protecting group; and complex peptides such as so-called glycopeptides having a sugar chain attached thereto.

Since it is believed that the minimum number of amino acids required for antibody recognition is four from the immunological point of view, the number of amino acids of the above described epitope peptide to the Crohn's disease antibody according to the present invention described above is four or more, but has no particular upper limit as long as it has a property of specifically binding to and recognizing the Crohn's disease antibody observed in patients with Crohn's disease. The number of amino acids is generally exemplified by from four to about 500 from the viewpoint of chemical synthesis such as peptide synthesis.

The salts of the peptides of the present invention include physiologically acceptable salts with acids or bases. Examples of such salts include salts with inorganic acids such as hydrochloric acid, phosphoric acid, hydrobromic acid and sulfuric acid; and salts with organic acids such as acetic acid, formic acid, propionic acid, fumaric acid, maleic acid, succinic acid, tartaric acid, citric acid, malic acid, oxalic acid, benzoic acid, methanesulfonic acid and benzenesulfonic acid. In addition, for example, salts with alkali metals such as sodium and potassium; salts with alkaline earth metals such as magnesium and calcium; salts with amines such as monomethylamine and triethylamine; salts with quaternary ammonium such as trimethylethylammonium and tetramethylammonium are included.

Hereinafter, preparation or production processes are described in detail in connection with the epitope peptide to the Crohn's disease antibody according to the present invention or a salt thereof (hereinafter, also referred to collectively as the epitope peptide to the Crohn's disease antibody) including a peptide having an amino acid sequence represented by any one of SEQ ID NOS: 1 to 3, or a salt thereof, as well as a peptide comprising a modified amino acid sequence of any one of SEQ ID NOS: 1 to 3 in which one or some (two or more) of the amino acids are substituted, deleted or added, and having a property of specifically binding to a Crohn's disease antibody, or a salt thereof.

2. Preparation of the Epitope Peptide to the Crohn's Disease Antibody

The epitope peptide to the Crohn's disease antibody according to the present invention can be obtained by a screening technique using a display phage library (a genome library, a cDNA library, or a random peptide library). Such a screening technique is called the phage display technique, and used by many of the skilled in the art as a known means for fusing a phage coat protein with a foreign antigenous epitope and expressing the epitope on the phage surface, followed by selection with a probe such as an antibody (Scott J. K. and Smith G. P., Science, 249, 386-390 (1990); Dybwad A., et al, Clin. Exp Immunol, 102, 438-442 (1995); Bluthner M., et al, J Immunol Methods, 198, 187-198 (1996)).

Phages used for libraries include filamentous phages (M13, f1, fd, 1f1, etc.: Smith G. P., et al, *Science,* 228, 1315-1317 (1985); Devlin J. J., et al., *Science,* 249, 404-406 (1990); Cwirla S. E., et al., *Proc. Natl. Acad. Sci. USA,* 87, 6378-6382 (1990)); λ phages (Maruyama I. N., et al., *Proc. Natl. Acad. Sci. USA,* 91, 8273-8277 (1994); Santi E., et al., *J. Mol Biol,* 296, 497-508 (2000)); and T7 phages (U.S. Pat. No. 5,766,905; Novagen T7 Select System Manual TB178 (2000)). Proteins as a library are induced to be expressed on the phage surface by cloning genomes, cDNAs or random oligonucleotides at the upstream or the downstream of the gene encoding a phage coat protein by use of a well-known gene manipulation technique to express them as capsid fusion proteins which can then be used as a genome library, a cDNA library, or a random peptide library, respectively.

Among specific methods for obtaining the epitope peptide to the Crohn's disease antibody using the screening technique, the following method using a cDNA library is suitable in the present invention.

First, total RNA is extracted from cultured cells such as colon cancer cells, and poly(A)$^+$ RNA is purified with an oligo(dT) column. From this, single strand cDNA is synthesized by using a random oligonucleotide (preferably with about eight bases) and reverse transcriptase. Then, double strand cDNA is synthesized by using RNaseH and *E. coli* DNA polymerase, is bonded to linker sequences, and is further digested with restriction enzyme to obtain double strand cDNA having cohesive ends. Finally, a phage DNA is cleaved by the same restriction enzyme and ligated with the above cDNA by DNA ligase so as to construct a cDNA library in accordance with in vitro packaging method.

The resulting cDNA library is added to a microplate, microbeads or the like to which the Crohn's disease patient serum antibody is in advance immobilized via Protein G or the like to capture phages specifically biding to the Crohn's disease patient serum antibody. There is no particular restriction on the Crohn's disease patient serum antibody to be immobilized to a microplate or the like as long as it is capable of at least binding to an antigen. For example, a serum itself collected from a patient with Crohn's disease can be used. Further, such a serum may be precipitated with an ammonium sulfate solution or purified with Protein A prior to use.

Phages not of interest that do not bind or only weakly bind thereto are removed by washing, and such procedure is repeated several times, and then the immobilized Crohn's disease patient serum antibody and the phages are dissociated by sodium dodecyl sulfate (hereinafter, abbreviated as SDS) or the like so that phages capable of binding to the Crohn's disease antibody in a Crohn's disease patient serum can be eluted.

In order to further select phages having a specificity to the Crohn's disease patient serum antibody, an *E. coli* host is infected with the above eluted phage suspension and allowed to form single plaques on an LB agar medium containing a protein expression inducer (isopropyl-β-D(-)-thiogalactopyranoside, etc.). These plaques are transferred to a nitrocellulose membrane, etc., and subjected to immunostain using a Crohn's disease patient serum, so that phages binding to the Crohn's disease patient serum antibody can be specified and isolated.

The resulting phages are immobilized to a microplate or the like via an anti-phage antibody and reacted with sera from Crohn's disease patients, from ulcerative colitis patients, and from healthy population, so that phages specifically reacting with the Crohn's disease patient serum antibody can be selected based on reactivity (hereinafter, referred to also as phage ELISA). Specifically, the above-obtained phages are immobilized by reacting them with an anti-phage antibody immobilized to a given support such as a microplate. The immobilized phages are reacted with sera from Crohn's disease patients as well as control sera such as sera from healthy population, sera from patients with ulcerative colitis or with other diseases such as autoimmune disease, colon cancer, acute enteritis, gastric ulcer and duodenal ulcer, so that phages that react specifically with the Crohn's disease patient sera can be selected based on reactivity.

From the phages selected by the phage ELISA screening described above, DNAs are extracted and purified, and base sequences of the inserted cDNAs can be determined by the dideoxy method or the like. Based on the resulting base sequence, an amino acid sequence can be determined, and thus the epitope peptide to the Crohn's disease antibody according to the present invention can be obtained by a general chemical synthesis and the like including peptide synthesis by liquid phase method or solid phase method.

Specifically, based on the determined amino acid sequence, chemical synthesis is possible by the stepwise elongation or fragment condensation method. Conventionally known methods can be used for removal, condensation and the like of the protecting group of amino acids used in the peptide synthesis, in order to prepare a peptide of interest. Examples include those methods described in the following publications: M. Bodanszky and M. A. Ondetti, "Peptide Synthesis", Interscience Publishers, New York, 1966; Schroeder and Luebke, "The Peptide", Academic Press, New York, 1965; Nobuo Izumiya, et al., "Pepuchido Gosei No Kiso To Jikken" in Japanese transliteration which means Foundation and Experiments of Peptide Synthesis, Maruzen, 1975; Haruaki Yajima and Shunpei Sakakibara, "Seikagaku Jikkenn Koza 1, Tanpakushitsu No Kagaku IV" in Japanese transliteration which means Biochemical Experiment Lecture 1, Protein Chemistry IV, 205, 1977; Haruaki Yajima, ed., "Zoku Iyakuhin No Kaihatsu Vol. 14, Pepuchido Gosei" in Japanese transliteration which means Sequel Drug Development, Vol. 14, Peptide Synthesis, Hirokawa Publishing.

Further, based on the determined amino acid sequence, artificially modified peptides wherein one or plural amino acids are substituted, deleted or added can be prepared. Specifically, they can be prepared by genetic engineering techniques such as site-specific mutagenesis and conventionally known chemical synthesis techniques such as the phosphoamidite method as described above. These modified peptides can be used as the epitope peptide to the Crohn's disease antibody according to the present invention.

Moreover, based on the determined amino acid sequence, homologous peptide sequences can be searched on databases. A highly homologous peptide or protein containing such a peptide can be prepared by a known molecular biological technique, which can be used as the epitope peptide to the Crohn's disease antibody according to the present invention.

The epitope peptide to the Crohn's disease antibody according to the present invention obtained as described above can be isolated and purified by a combination of conventionally known protein or peptide separation and purification methods. These known separation and purification methods include ones using solubility such as salt precipitation and solvent precipitation; ones using mainly molecular weight difference such as dialysis, ultrafiltration and gel filtration; ones using charge difference such as ion exchange chromatography and SDS polyacrylamide gel electrophoresis; ones using specific affinity such as affinity chromatography; ones using hydrophobicity difference such as reverse phase high performance liquid chromatography; and ones using difference in isoelectric point such as isoelectric focusing. Further, the amino acid composition of a purified peptide can be readily measured and analyzed by using an amino acid analyzer.

When a peptide obtained by the above method is of free form, it can be converted into a suitable salt by a known method or a method equivalent thereto. On the contrary, when a peptide is obtained as a salt, it can be converted into a free form or another salt by a known method or a method equivalent thereto.

3. A Test Reagent, a Test Kit, and a Test Method for Crohn's Disease

The above-obtained epitope peptide to the Crohn's disease antibody has a property of specifically binding to the Crohn's disease antibody in sera of Crohn's disease patients. Taking advantage of such a biding property, a test reagent, a test kit, and a test method for Crohn's disease are provided, which employ such a peptide as an active ingredient.

Specifically, there are provided 1) a test reagent for Crohn's disease, comprising an above-described epitope peptide to the Crohn's disease antibody as an active ingredient; 2) a test kit for Crohn's disease, comprising the test reagent described in the above 1); 3) a test method for Crohn's disease, comprising a step of detecting an absence or presence of an antibody specifically binding to at least one peptide of the above epitope peptides to the Crohn's disease antibody or a salt thereof in a biological specimen; and 4) a test method for Crohn's disease, comprising a step of using the above test reagent or test kit.

1) A Test Reagent for Crohn's Disease

When the above epitope peptide to the Crohn's disease antibody is used as an active ingredient, the specific active ingredient is at least one peptide or a salt thereof selected from the group consisting of (a) a peptide comprising an amino acid sequence represented by any one of SEQ ID NOS: 1 to 3 or a salt thereof; and (b) a peptide or a salt thereof, wherein the peptide comprises a modified amino acid sequence represented by SEQ ID NOS: 1 to 3 in which one or more amino acids are substituted or supplemented with another amino acid or deleted, or comprises a part of such an amino acid sequence, and has a property of specifically binding to the antibody in sera of patients with Crohn's disease.

As the active ingredient of the test reagent for Crohn's disease, the above epitope peptides to the Crohn's disease antibody can be used singly or in any combination of two or more.

The test reagent for Crohn's disease according to the present invention can be used as an antigen specifically binding to the Crohn's disease antibody so that detection, capture and the like of the Crohn's disease antibody can be carried out. For covering the scope of these purposes, the active ingredient may be not only the above epitope peptides to the Crohn's disease antibody, but also a labeled form (a labeled peptide) wherein the peptide is labeled with a certain labeling compound. In addition, the test reagent may contain other components.

As the compound labeling the above peptides, a labeling compound usually used in the art can be used, and specific examples thereof include radioisotopes such as $^{3}H$, $^{14}C$, $^{131}I$, and $^{99m}Tc$; enzymes such as β-galactosidase, β-glucosidase, alkaline phosphatase, peroxidase and malate dehydrogenase; fluorescent substances such as fluorescamine and fluorescein isothiocyanate; and luminescent substances such as luciferin, luminol derivatives and isoluminol derivatives.

By using a peptide of the present invention, which is labeled with an enzyme, a radioisotope or the like, detection, capture and the like of the Crohn's disease antibody can be carried out. In addition, as will be described in detail later, a peptide of the present invention can also be used without labeling as a test reagent utilizing, for example, an immunoassay such as radioimmunoassay and enzyme immunoassay.

2) A Kit for Crohn's Disease

When Crohn's disease is tested by using a biological specimen such as blood (serum or plasma) of a subject, it is easy and convenient to make use of a test kit containing the above reagent that comprises the epitope peptide to the Crohn's disease antibody as an active ingredient.

The test kit for Crohn's disease according to the present invention can use not only an epitope peptide to the Crohn's disease antibody according to the present invention, but also a labeled form (a labeled peptide) wherein the peptide is labeled with a certain labeling compound as described above, as long as the test kit contains the above test reagent in order to allow the reagent bind to the Crohn's disease antibody. Further, the peptide can be used in an immobilized form by immobilizing the peptide to a given support (a solid phase) in advance.

In addition to the above reagent, a test kit for Crohn's disease according to the present invention can optionally use other reagents depending on types of immunoassay and detection methods employed or adapted for the Crohn's disease test that will be described later. For example, when the epitope peptide to the Crohn's disease antibody is used in a form labeled with a radioisotope, a radioactivity detection device such as a liquid scintillation counter is required; and when it is used in a form labeled with an enzyme, a fluorescent substance or a luminescent substance, a corresponding detection device is required. Therefore, a detection reagent, a solvent, a base material and the like required for each purpose are contained as other ingredients in the present test kit.

Especially, the test kit of the present invention preferably contains a secondary antibody (anti-human IgG antibody, e.g., anti-human IgG mouse antibody) for detecting human immunoglobulin (also called human IgG), as an ingredient other than the above test reagent that comprises the above epitope peptide to the Crohn's disease antibody as an active ingredient. The anti-human IgG antibody may be labeled with a labeling compound described above, or may be immobilized to a given support (a solid phase) in advance.

In addition, the test kit may include an enzyme substrate or an enzyme required by a labeling compound; a detecting reagent for detecting a reaction between the labeling compound and the enzyme substrate; and others for conducting measurement conveniently, including various suitable samples, diluting solutions for the reagents, the secondary antibody or the like, a standard antibody, a buffer solution, a washing solution, an enzyme substrate solution, and a reaction termination solution. Further, when the above test reagent or anti-human IgG antibody is not labeled or immobilized, the test kit can include an above-described labeling compound or support (solid phase) as another component.

The test kit for Crohn's disease according to the present invention is a combination of the above test reagent that comprises the epitope peptide to the Crohn's disease antibody as an active ingredient (which peptide may be immobilized and/or labeled), with at least one arbitrarily selected from an anti-human IgG antibody (which is the secondary antibody that may be immobilized and/or labeled); a substrate required by a labeling compound (an enzyme substrate when the labeling compound is an enzyme; an enzyme when the labeling compound is a fluorescence substance or a luminescent substance, etc.); an antibody diluting solution; a standard antibody; a buffer solution; a washing solution; an enzyme substrate solution; a reaction termination solution; a support (a solid phase); and a labeling compound. In the test kit for Crohn's disease according to the present invention, it is preferable to use an enzyme as the labeling compound from the viewpoint of operability, safety, sensitivity and accuracy of measurement, and the like.

3) A Test Method for Crohn's Disease

In the test method for Crohn's disease according to the present invention, a biological specimen of a subject can be used as a sample to examine whether each subject is affected by Crohn's disease. Specifically, whether each subject is affected by Crohn's disease is examined using, as a marker, a certain antibody that is specifically present in biological specimens of Crohn's patients. The sample includes various biological specimens such as blood (serum or plasma), urine, sweat, saliva, semen and spinal fluid of a (human) subject, and is preferably a serum or plasma.

The test method for Crohn's disease according to the present invention is characterized in that the above epitope peptide to the Crohn's disease antibody is used as an antigen substance. Specifically, when the Crohn's disease antibody is present in a subject's biological specimen, it forms a complex with the Crohn's disease antibody epitope peptide as an antigen due to antigen-antibody reaction. By detecting and measuring such a complex, occurrence or non-occurrence of Crohn's disease and the like are diagnosed.

Methods for detecting the complex produced by the reaction between the Crohn's disease antibody epitope peptide as the antigen and the Crohn's disease antibody characteristic of Crohn's disease patients may be conventionally known methods. Examples thereof include radioimmunoassay, enzyme immunoassay, immunochromatography, and the like. When these immunological assays are used for the test method of the present invention, no special conditions, operations or the like are required. The measuring system can be constructed by using usual conditions and operations of each technique together with general technological considerations given by the skilled in the art. For detailed description of such general techniques, reviews and books can be referenced. For example, Hiroshi Irie, ed., "Radioimmunoassay" (Kodansha, 1964); Hiroshi Irie, ed., "Sequel Radioimmunoassay" (Kodansha, 1979); Eiji Ishikawa, et al., ed., "Koso Meneki Sokuteiho" in Japanese transliteration which means Enzyme Immunoassay (Igakushoin, 1978); Eiji Ishikawa, et al., ed., "Koso Meneki Sokuteiho" in Japanese transliteration which means Enzyme Immunoassay (2nd ed.) (Igakushoin, 1982); Eiji Ishikawa, et al., ed., "Koso Meneki Sokuteiho" in Japanese transliteration which means Enzyme Immunoassay (3rd ed.) (Igakushoin, 1987) can be referenced.

Further, in the test method for Crohn's disease according to the present invention, the above test reagent or test kit that comprises, as an active ingredient, the above epitope peptide to the Crohn's disease antibody is preferably used.

Specifically, as the test method for Crohn's disease according to the present invention, various immunological assays can be employed utilizing the above epitope peptide to the Crohn's disease antibody as an antigen substance. For example, referring to a solid-phase, enzyme-linked immunosorbent assay (hereinafter, also called ELISA) using a human serum as a sample, the Crohn's disease antibody to be examined can be detected and measured by the following method.

First, the above Crohn's disease antibody epitope peptide as the antigen substance is immobilized to a support or the like, to which a biological specimen as a sample is added. If the Crohn's disease antibody is present in the sample, it binds to the immobilized peptide. Then, the Crohn's disease antibody present in the sample can be detected and measured by conducting a second antigen-antibody reaction, detection and the like using a detection reagent such as an anti-human IgG antibody (the secondary antibody including one labeled with a labeling substance) specifically biding to human IgG.

Alternatively, a detection reagent, such as an anti-human IgG antibody, may be immobilized to the support in advance, to which a sample is added so that the Crohn's disease antibody in a biological specimen is captured. Then, by adding the above Crohn's disease antibody epitope peptide as the antigen substance, the Crohn's disease antibody present in the sample can also be detected and measured. Selection of various means for these assay techniques, modifications thereof, and the like are well-known to the skilled in the art, and thus all of them can be used in the present invention (see "Rinsho Kensaho Teiyo" in Japanese transliteration which means Clinical Test Methods Synopsis, Kanehara, 1995; etc.).

There is no particular restriction on detection reagents such as an anti-human IgG antibody for detecting the Crohn's disease antibody, and various commonly used commercially available reagents can be used. For example, anti-human IgG antibodies binding specifically to human IgG are preferably used, which can be obtained by sensitizing nonhuman species such as mouse, rabbit, goat and pig with human IgG as an antigen. These anti-human IgG antibodies and human IgG can be labeled with a labeling compound described above. The labeling compound used for this labeling purpose includes labeling compounds described above. Particularly, those labeled with such labeling compounds as enzymes are preferred. These labeled anti-human IgG antibodies and human IgGs are commercially available, but can be prepared in accordance with ordinary methods.

In the test method for Crohn's disease according to the present invention, enzyme immunoassays such as ELISA which uses an enzyme as a labeling compound as described above, are preferably employed from the viewpoints of operability, safety, measurement sensitivity and accuracy, and the like. Labeling compounds for the enzyme labeling include those described above. Further, labeling methods using these enzyme-labeling compounds can be conventionally known methods (Eiji Ishikawa, et al., "Koso Meneki Sokuteiho" in Japanese transliteration which means Enzyme Immunoassay, 2nd ed., Igakushoin, 1982; etc.).

Further, when a solid phase method is employed in the above assay, there is no particular restriction on supports as long as they are insoluble and inert carriers, and usually-employed ones can be widely used. Examples thereof include microplates, beads, membranes, sticks, test tubes and the like, which are made of such materials as glass, Sephadex®, Sepharose®, and plastic resins (polystyrene, polypropylene, polycarbonate, etc.).

Moreover, the epitope peptide to the Crohn's disease antibody according to the present invention as the antigen or the anti-human IgG antibody as the secondary antibody can be made insoluble by physical adsorption. They may also be made insoluble by a method relying on chemical bonding which is generally employed to render proteins, enzymes or the like insoluble or immobilized.

In the above ELISA, a sample is reacted with the immobilized epitope peptide to the Crohn's disease antibody (the primary reaction), and then the labeled anti-human IgG antibody is reacted therewith (the secondary reaction) followed by measurement of activity of the labeled compound on the immobilized carrier. The Crohn's disease antibody contained in the sample can be thereby detected or quantified. The primary reaction and the secondary reaction can be performed at the same time or at a certain interval. Methods for labeling and immobilizing can be similar to those described above. Further, in the immunoassay by ELISA, the antibody immobilized on the support or the labeled antibody should not be necessarily one kind, but may be a mixture of two or more kinds of antibodies for the purpose of increasing sensitivity of measurement, etc.

Solvents used in the above measurement system may be usually employed ones, as long as they do not affect the reactions, and examples thereof include buffer solutions of about pH 6 to 9 such as a phosphate buffer solution (hereinafter, abbreviated as PBS), a borate buffer solution, a tris-HCl buffer solution, a citrate buffer solution and an acetate buffer solution; and these buffer solutions containing a surfactant such as Tween® 20 and Triton®-100, a stabilizer such as bovine serum albumin (hereinafter, abbreviated as BSA) and milk protein, or a preservative such as $NaN_3$.

There is also no restriction on immune reaction conditions, and usual conditions generally used for immunoassays are adapted. In general, the conditions may be at a temperature of about from 4 to 40° C. for about from 0.5 to 24 hrs.

In the above procedures, assay for the complex (including one in a form labeled with a labeled compound) resulting from the antigen-antibody reaction can be carried out by a method suitable for the type of the labeling compound in use. For example, when the labeling compound is an enzyme, enzyme activity of the labeled form can be measured in accordance with a known method suitable for the type of the enzyme in use.

The assay for such enzyme activity can be carried out by a widely-used method in which a substrate suitable for the enzyme, for example, 3,3',5,5'-tetramethylbenzidine (abbreviated as TMB) or o-phenylenediamine (abbreviated as OPD) for peroxidase; or p-nitrophenylphosphate (abbreviated as pNPP) for alkaline phosphatase is added and reacted for a given length of time, followed by measurement of generated color by a spectrophotometer or the like.

The test method for Crohn's disease according to the present invention is summarized below:

<1> The epitope peptide to the Crohn's disease antibody as an antigen is immobilized in each well of a microplate. Usually, nonspecific binding sites in the well are blocked with a protein such as BSA and casein or a surfactant such as Tween® 20 brand surfactant;

<2> Samples (sera or plasma specimens) are diluted with a buffer solution (a sample diluting solution) optionally containing a protein such as BSA and casein or a surfactant such as Tween® 20 brand surfactant, and then added to the above immobilized microplate to thereby effect antigen-antibody reaction (the primary reaction);

<3> The microplate is washed with a buffer solution (a washing solution) preferably containing a surfactant such as Tween® 20 brand surfactant, and then the labeled anti-human IgG antibody is diluted with a buffer solution (the diluting solution) containing a protein such as BSA and casein or a surfactant such as Tween® 20 brand surfactant, and added thereto to effect antigen-antibody reaction (the secondary reaction); and <4> After the microplate is washed with the above washing solution, an assay suitable for the label is carried out, that is, radioactivity is measured for radiolabeling, and enzyme activity is measured for enzymatic labeling.

Hereinafter, working examples are illustrated to explain the present invention further in detail, but the present invention should not be construed to be limited to these examples.

Example 1

Selection and Identification of Epitope Peptides to the Crohn's Disease Antibody 1) Preparation of a cDNA Phage Display Library Using T7 Phage Total RNA was extracted and purified from about 108 cultured cells of Caco-2 (Human colon carcinoma; RIKEN CELL BANK) by using an RNA extraction kit from Qiagen to obtain 654 μg of the total RNA. By using an oligo(dT)-cellulose column, 22.8 μg of poly $(A)^+$ RNA was purified from 600 μg of the total RNA, and then single strand cDNA was synthesized using a random oligomer (nnnnnnCG) and reverse transcriptase (Omni-RT from Qiagen).

Then, by using RNaseH and *E. coli* DNA polymerase I, double strand cDNA was synthesized, which was then end-blunted by T4 DNA polymerase. After the cDNA was methylated by methylase, linker sequences (18 mer oligoDNA) were ligated by T4 DNA ligase, and further the ends of the cDNA was cleaved by restriction enzymes (EcoRI and NotI) followed by gel filtration with a spin column (from Clontech) to remove unreacted linkers and cleaved small fragments.

A T7 phage vector (from Novagen) was cleaved by the same restriction enzymes, to which the cDNA fragments obtained above were ligated by T4 DNA ligase. This ligation solution and a T7 phage in vitro packaging kit (from Novagen) were used to form phage particles, with which then host *E. coli* BLT 5615 was infected to allow it to amplify. A cDNA library having a size of about $1.3 \times 10^7$ was prepared.

2) Screening for Antigen Phages Binding to the Crohn's Disease Patient Serum Antibody A single colony of host *E. coli* BLT 5615 was inoculated into an LB medium containing 50 μg/ml ampicillin to conduct culture at 37° C. until the turbidity at 600 nm became 0.5. To this *E. coli* culture solution, isopropyl-β-D(−)-thiogalactopyranoside (hereinafter abbreviated as IPTG) was added at the final concentration of 1 mM to conduct culture at 37° C. for 30 min. Then, the cDNA library prepared in 1) or a commercially available cDNA library derived from colon cancer was added thereto to continue the culture at 37° C. until complete lysis occurred. Immediately after lysis, the mixture was cooled on ice, followed by centrifugation to remove lysed cell fragments, and thereby a supernatant was obtained. To this supernatant, a milk buffer (a 25 mM tris-HCl buffer (containing 137 mM NaCl, and 2.68 mM KCl; pH 7.4) (hereinafter, abbreviated as TBS) containing 5% skim milk and 0.1% Tween® 20) of the equivalent volume was added to obtain a lysed phage solution that was used in the following procedure.

To a microplate (from Dynatec Lab.), Protein G (from Sigma) diluted with PBS to 20 μg/ml was added to react at 4° C. overnight. After the reaction, the microplate was washed with a milk buffer, and then blocked with the same buffer to prepare a Protein G-bound plate.

Serum samples were obtained from 21 Crohn's disease patients. From the serum pool, the serum equivalent in volume to one to three patients' samples was obtained and diluted with PBS containing 0.05% NaN$_3$, which was then added to the Protein G-bound plate. The plate was allowed to stand still at 22° C. for 2 hrs., so that antibodies in the serum were bound to the plate, followed by washing with a milk buffer three times to prepare a Crohn's disease patient serum antibody-bound plate.

To the Crohn's disease patient serum antibody-bound plate, the above lysed phage solution (a phage titer of about 1×10$^{11}$ pfu) was added, which was then gently shaken at room temperature for 3 hrs. to allow antibody expressing phages to bind thereto. The plate was washed with a milk buffer and TBS to remove unbound phage suspension, and then PBS containing 0.5% SDS was added and shaken at room temperature for 20 min. to elute the bound phages, and thereby a phage eluate was obtained.

3) Immunostaining of Phage Plaques and Isolation of Antigen Phages Binding to the Crohn's Disease Patient Serum Antibody With the thus-obtained phage eluate, host *E. coli* BLT5615 was infected, which was then inoculate onto an LB agar medium containing 50 µg/ml ampicillin and 1 mM IPTG to conduct culture at 37° C. for 3 hrs., and thereby plaques were formed. The resulting plaques were allowed to stand still at 4° C. for 1 hr., which was then covered with a nitrocellulose membrane (from Osmonics). The membrane was allowed to stand still at room temperature for 5 min. to transfer the phage particles thereto.

The membrane was blocked with a milk buffer, and then soaked into a Crohn's disease patient serum diluted with the same buffer, which was then gently shaken at 4° C. overnight. This membrane was washed with a milk buffer three times, and then soaked in a solution in which alkaline phosphatase-labeled anti-human IgG monoclonal antibodies (from Sigma) were diluted to 1/5000 with the same buffer, followed by being gently shaken at room temperature for 1 hr.

This membrane was washed with a milk buffer three times, then washed with 100 mM tris-HCl (containing 100 mM NaCl and 5 mM MgCl$_2$; pH 9.5) (hereinafter, abbreviated an AP buffer), and then soaked into an AP buffer containing a chromogenic solution (0.33 mg/ml nitrobluetetrazolium (hereinafter, abbreviated as NBT) and 0.165 mg/ml bromochloroindolylphosphate (hereinafter, abbreviated as BCIP)) so that color was generated at room temperature.

Immunostained isolated phage plaques were scraped off and suspended in an LB medium containing 50 µg/ml ampicillin. A part thereof was added to a host *E. coli* BLT5615 culture solution to conduct culture at 37° C. until complete lysis occurred. This lysed solution was centrifuged to remove lysed cell fragments, and the resultant supernatant was supplemented with CHCl$_3$ at the final concentration of 0.3%. This was stored at 4° C. as a solution of cloned antigen phages binding to the Crohn's disease patient serum antibody.

4) Phage ELISA

To a host *E. coli* BLT5615 culture solution, the antigen phages binding to the Crohn's disease patient serum antibody obtained in the above 3) was added to conduct culture at 37° C. until complete lysis occurred. This solution was centrifuged to remove lysed cell fragments, and the resultant supernatant was supplemented with four times volume of a milk buffer. The resultant solution was used for the primary reaction in the following procedure.

To a microplate, anti-T7 phage antibodies (rabbit polyclonal antibodies) diluted with PBS to 1 µg/ml was added to react at 4° C. overnight. After the reaction, the microplate was washed with a milk buffer, and then blocked with the same buffer to prepare an anti-T7 phage antibody-bound plate.

The above solution for the primary reaction was added to the anti-T7 phage antibody-bound plate and gently shaken at 22° C. for 2 hrs., so that the phages were bound to the plate, followed by washing with a milk buffer three times. Various sera (derived from Crohn's disease patients, ulcerative colitis patients, or healthy people) that were diluted to 1/250 with the same buffer were added thereto and allowed to stand still at 22° C. for 1 hr., and then washed with the same buffer six times. A solution in which alkaline phosphatase-labeled anti-human IgG monoclonal antibodies were diluted to 1/5000 with the same buffer was added thereto and allowed to stand still at 22° C. for 1 hr., and then washed with the same buffer six times. Further, the plate was washed with an AP buffer, and then supplemented with a p-nitrophenylphosphate solution (from Sigma) to effect reaction at 22° C. for 40 min. A termination solution (2N NaOH) was added to terminate the reaction, and then absorbance (at 405 nm) was measured by a plate reader to compare antibody titers in the sera. From the results of reactivity, three clones (as a matter of convenience, abbreviated as CD#47, CD#336, and CD#353) that exhibited high specificities to the Crohn's disease patient sera were selected.

5) Determination of DNA Base Sequences Encoding the Antigen Peptides and Amino Acid Sequences With the above three antigen phages binding to the Crohn's disease patient serum antibody selected by the phage ELISA, host *E. coli* BLT5615 was infected and then lysed. From the resulting lysed solutions, phage DNAs were extracted using Quiagen lambda kits (from Quiagen). Inserted cDNA base sequences of the phage DNAs were determined by the dideoxy method. The amino acid sequence of each of the clones determined based on the respective inserted cDNA base sequence is shown in Table 1 using a single letter code.

TABLE 1

| Clone name | Amino acid length | Amino acid sequence | SEQ ID NO: |
|---|---|---|---|
| CD#47 | 27 | NSVKNEVEEVTFTKHTQCLGCFKSGFS | 1 |
| CD#336 | 26 | VIPALSEAEAGGSPEVRSSRPAWPIW | 2 |
| CD#353 | 8 | MIRGLFPN | 3 |

Each linear peptide having the amino acid sequence of each of the clones (as a matter of convenience, abbreviated as TCP-47, TCP-336, and TCP-353) was synthesized and purified (by Sigma Genosis upon request). These peptides were used as epitope peptides to the Crohn's disease antibody in the following experiments. The properties of each of the prepared peptides are shown in Table 2.

TABLE 2

| Peptide name | Amino acid length | Molecular weight | Purity | Isoelectric point | Hydrophobicity |
|---|---|---|---|---|---|
| TCP-47 | 27 | 3023.3 | 92.3% | 6.97 | 33.3% |
| TCP-336 | 26 | 2763.1 | 99.7% | 4.61 | 65.4% |
| TCP-353 | 8 | 947.2 | 91.0% | 10.9 | 75.0% |

In Table 2, the unit of molecular weight is kDa; purity is expressed by an area ratio based on analysis by liquid chromatography (absorbance at 225 nm); and hydrophobicity is a percentage of the hydrophobic amino acid content.

Example 2

Reactivity of TCP-47, TCP-336 and TCP-353 with Various Serum Samples

ELISA was performed using the epitope peptides to the Crohn's disease antibody obtained in Example 1 as antigens to study reactivity with various sera (from Crohn's disease patients, ulcerative colitis patients, or healthy people).

To a microplate, each of the peptides diluted with PBS to 2 µg/ml was added and reacted at 4° C. overnight. After the reaction, the microplate was washed with a blocking buffer (PBS containing 2% BSA, 5% sucrose, and 0.1% $NaN_3$) followed by blocking with the same buffer to prepare a peptide-immobilized plate.

To a peptide-immobilized plate, various sera (Crohn's disease patient sera: 32 samples, ulcerative colitis patient sera: 32 samples, and healthy people sera: 32 samples) that were diluted to 1/100 with a sample diluting solution (PBS containing 1% BSA and 0.1% Tween® 20) were added and allowed to stand still at 22° C. for one hour, followed by washing with a washing buffer (PBS containing 0.1% Tween® 20) six times. Then, an HRP-labeled anti-human IgG antibody (from Dako) diluted to 1/4000 with the same buffer was added thereto and allowed to stand still at 22° C. for 1 hr., followed by washing with the same washing buffer eight times. A TMB solution (from Dako) as a chromogenic substrate was further added thereto and allowed to react at 22° C. for 3C min., and then a termination solution (2N $H_2SO_4$) was added to terminate the reaction, followed by measurement of absorbance (at from 450 to 600 nm) by a plate reader. The results of measurement are shown in FIG. 1 as a scatter diagram.

Based on these results, a significance test was carried out. Significantly higher reactivity with the Crohn's disease patient serum was indicated by all of the three peptides, as compared with the ulcerative colitis patient serum or the healthy person serum. The cut-off values were determined as described below, and by using these, positive reactions were evaluated to calculate the positive percentage for the various sera. The results are shown in Table 3.

Cut-Off Values:

TCP-47, OD=0.40: the OD value that gives the highest sensitivity in the range of 0.1 or less of 1-specificity on the Receiver Operating Characteristic (ROC) curve.

TCP-336, OD=1.10: the same as above.

TCP-353, OD=0.11: the average of the measured values of the sera from the healthy people plus 2SD.

TABLE 3

| | | TCP-47 | TCP-336 | TCP-353 |
|---|---|---|---|---|
| Positive percentage | Crohn's disease patients (32) | 40.6% (13) | 28.1% (9) | 53.1% (17) |
| False positive percentage | Ulcerative colitis patients (32) | 0% (0) | 3.1% (1) | 3.1% (1) |
| | Healthy people (32) | 9.4% (3) | 9.4% (3) | 6.3% (2) |

In the table, the numeral in parenthesis indicates the number of samples.

As shown in Table 3, the positive percentage for the Crohn's disease patient sera indicated by TCP-47, TCP-336, and TCP-353 is 40.6%, 28.1%, and 53.1%, respectively, whereas the false positive percentage for the ulcerative colitis patient sera and the healthy people sera was from 3.1 to 9.4%. These results demonstrate that these peptides specifically bind to antibodies in the Crohn's disease patient sera.

Example 3

Measurement of Various Many Serum Samples by ELISA with TCP-353

TCP-353, whose positive percentage for the Crohn's disease patient sera was the highest (53.1%) and false positive percentage for the ulcerative colitis patient sera or for the healthy people sera was low (6.3% and 3.1%, respectively) in Example 2, was used to measure various many serum samples (Crohn's disease patient sera: 60 samples, ulcerative colitis patient sera: 109 samples, healthy people sera: 71 samples, acute enteritis patient sera: 11 samples, colon cancer patient sera: 35 samples, and chronic liver disease patient sera: 49 samples).

Measurement was carried out in the same manner as in Example 2 except that the serum was diluted to 1/400. Further, by using a standard solution prepared by pooling positive patient sera, a standard curve was drawn, and the resulting absorbance values were converted into unit values. Results of measurement are shown in FIG. 3 as a scatter diagram.

Based on these results, a significance test was carried out. Significantly higher reactivity of TCP-353 was shown with the Crohn's disease patient sera than the ulcerative colitis patient sera, the healthy people sera, the acute enteritis patient sera, the colon cancer patient sera, and the chronic liver disease patient sera.

Further, the number of positive patient sera and the positive percentage thereof are shown in Table 4, provided that the cut-off value was set to be a value of the average of the measured values of the 71 healthy people serum samples plus 3SD.

TABLE 4

| | | Number of positive sera | Percentage (%) |
|---|---|---|---|
| Positive percentage | Crohn's disease patients (60) | 37 | 61.7% |
| False positive percentage | Ulcerative colitis patients (109) | 8 | 7.3% |
| | Healthy people (71) | 2 | 2.8% |
| | Acute enteritis patients (11) | 0 | 0% |
| | Colon cancer patients (35) | 4 | 11.4% |
| | Chronic liver disease patients (49) | 4 | 8.2% |

In the table, the numeral in parenthesis indicates the number of samples.

As shown in Table 4, the positive percentage for the Crohn's disease patient sera is 61.7% (37/60), whereas the false positive percentage for the ulcerative colitis patient sera, the healthy people sera, the acute enteritis patient sera, the colon cancer patient sera, and the chronic liver disease patient sera, is 7.3% (8/109), 2.8% (2/71), 0% (0/11), 11.4% (4/35), and 8.2% (4/49), respectively. These results demonstrate that the present test method can be used to detect occurrence and non-occurrence of Crohn's disease and distinguish Crohn's disease from other related diseases, in particular, ulcerative colitis.

Example 4

Comparison Between ELISA with TCP-353 and ASCA-IgG ELISA

The reactivity of the anti-baker's yeast antibody (abbreviated as ASCA-IgG), which has been reported to be related to Crohn's disease (Gut, 1998, 42, 788-791; Am J. Gstroenterol., 2000, 95, 359-367; Am J. Gastroenterol., 2001, 96, 730-734), with various sera was studied, and was compared with ELISA using TPC-353 (hereinafter, also called TCP-353 ELISA) in terms of usefulness in diagnosis of Crohn's disease.

The measurement by ELISA using ASCA-IgG (hereinafter, referred to also as ASCA-IgG ELISA) was conducted by using a kit from GENESIS Diagnostics in accordance with the instruction manual thereof. The results of measurement are shown in FIG. 4 as a scatter diagram. The cut-off value was predetermined in ASCA-IgG ELISA so that the specificity was 90%, and the reactivity percentage was obtained for each serum. The results by comparison in the positive percentage between ASCA-IgG ELISA and TCP-353 ELISA are shown in Table 5.

In addition, the measured values of the Crohn's disease patient sera by ASCA-IgG ELISA and by TCP-353 ELISA are plotted along the vertical and horizontal axes, respectively, to obtain a correlation coefficient and look for absence or presence of correlation between the two measuring systems. The results are shown in FIG. 5.

TABLE 5

| | | ASCA IgG | TCP-353 |
|---|---|---|---|
| Sensitivity | Crohn's disease patients (60) | 31.7% | 61.7% |
| Specificity | | 90.9% | 93.5% |
| False positive percentage | Ulcerative colitis patients (109) | 8.3% | 7.3% |
| | Healthy people (71) | 8.5% | 2.8% |
| | Acute enteritis patients (11) | 9.1% | 0% |
| | Colon cancer patients (35) | 5.7% | 11.4% |
| | Chronic liver disease patients (49) | 14.3% | 8.2% |
| Positive predictive value (PPV) | | 43.2% | 67.3% |
| Negative predictive value (NPV) | | 85.9% | 91.8% |
| Diagnosis efficiency (sensitivity × specificity) | | 0.288 | 0.576 |

In the table, the numeral in parenthesis indicates the number of samples.

In Table 5:

Sensitivity is a value calculated by the following formula: (the number of positive sera from Crohn's disease patients)/(the number of sera from Crohn's disease patients measured)×100;

Specificity is a value calculated by the following formula: {1−(the number of positive sera from non-Crohn's disease patients)/(the number of sera from non-Crohn's disease patients and healthy people measured)}×100;

A positive predictive value (PPV) is a value calculated by the following formula: (the number of positive sera from Crohn's disease patients)/(the number of all positive sera)×100; and A negative predictive value (NPV) is a value calculated by the following formula: (the number of negative sera from non-Crohn's disease patients)/(the number of all negative sera)×100.

The results of FIG. 4 and Table 5 show that ELISA using TCP-353 is superior to ASCA-IgG ELISA in both sensitivity and specificity, and also has higher positive and negative predictive values, indicating greater accuracy in diagnosis. In addition, the correlation coefficient obtained from FIG. 5 is 0.229, indicating no correlation between the two assay systems, which suggests that a different antibody is measured by each system.

Example 5

Comparison with Known Branched Peptides Binding to a Crohn's Disease Antibody Four kinds of branched peptides (abbreviated as cocktail-MAP; Wo 02/088175 A1) that are peptides binding to a Crohn's disease antibody were prepared for comparison with the ELISA using TCP-353 in terms of usefulness in diagnosis of Crohn's disease.

ELISA using cocktail-MAP (referred to also as cocktail-MAP ELISA) was conducted according to the international publication (WO 02/088175A1), except that the same standard solution as that employed in TCP-353 ELISA was used, and the measured absorbance values were converted into Index values. The results of measurement are shown in FIG. 6 as a scatter diagram. In addition, the cut-off value was set to be the value of the average of the measured values of the 71 healthy people serum samples plus 3SD, whereby the reactivity percentage was obtained for each serum.

The results by comparison in the positive percentage between cocktail-MAP ELISA and TCP-353 ELISA are shown in Table 6. In addition, the measured values of the Crohn's disease patient sera by cocktail-MAP ELISA and by TCP-353 ELISA are plotted along the vertical and horizontal axes, respectively, to obtain a correlation coefficient and look for absence or presence of correlation between the two measuring systems. The results are shown in FIG. 7.

TABLE 6

| | | cocktail MAP | TCP-353 |
|---|---|---|---|
| Sensitivity | Crohn's disease patients (60) | 55.0% | 61.7% |
| Specificity | | 92.0% | 93.5% |
| False positive percentage | Ulcerative colitis patients (109) | 8.3% | 7.3% |
| | Healthy people (71) | 4.2% | 2.8% |
| | Acute enteritis patients (11) | 9.1% | 0% |
| | Colon cancer patients (35) | 5.7% | 11.4% |
| | Chronic liver disease patients (49) | 14.3% | 8.2% |
| Positive predictive value (PPV) | | 60.0% | 67.3% |
| Negative predictive value (NPV) | | 90.4% | 91.8% |
| Diagnosis efficiency (sensitivity × specificity) | | 0.506 | 0.576 |

In the table, the numeral in parenthesis indicates the number of samples. PPV, NPV, etc. are as defined in Table 5.

The above results suggest that ELISA using TCP-353 is better than cocktail-MAP ELISA in sensitivity, specificity, and accuracy in diagnosis. Moreover, the correlation coefficient obtained from FIG. 7 is 0.281, indicating no correlation between the two measuring systems, which suggests that a different antibody is measured by each system.

Example 6

Homology Search for the Epitope Peptides to the Crohn's Disease Antibody

For the amino acid sequences of the obtained epitope peptides to the Crohn's disease antibody (TCP-47, TCP-336, and TCP-353), the BLAST search was carried out to look for peptides or proteins having homologous amino acid sequences. The results are shown in FIGS. 8, 9, and 10. TCP-47 is identical with the C-terminal region of the Titin protein from human or fruit fly, and also homologous proteins are found from viruses, bacteria, molds, and protozoan. TCP-336 matches to a great extent with a human protein. TCP-353 is identical to a protein from Oryza sativa, suggesting a relation between Crohn's disease and an alimentary antigen.

Industrial Applicability

The epitope peptide to the Crohn's disease antibody according to the present invention and the test reagent using the same peptide make it possible to determine occurrence and non-occurrence of Crohn's disease conveniently, rapidly and accurately, and thus can be utilized for a diagnostic reagent and a test method which are both extremely useful in diagnosis of Crohn's disease.

BRIEF DESCRIPTION OF THE DRAWINGS

FIG. 8 shows proteins (SEQ ID NOS 5, 7, 9, 11, 13, 14, 16, 18 and 20, respectively, in order of appearance) homologous in amino acid sequence to TCP-47 (SEQ ID NOS 4, 6, 8, 10, 12, 12, 15, 17 and 19, respectively, in order of appearance), which were found on protein databases by the BLAST search. In the figure, | indicates that amino acids are matched, and : indicates that amino acids are similar.

FIG. 9 shows proteins (SEQ ID NOS 22-24, respectively, in order of appearance) homologous in amino acid sequence to TCP-336 (SEQ ID NOS 21, 2 and 2 respectively, in order of appearance), which were found on protein databases by the BLAST search. In the figure, | indicates that amino acids are matched, and : indicates that amino acids are similar.

FIG. 10 shows proteins (SEQ ID NOS 26-27 and 29-30, respectively, in order of appearance) homologous in amino acid sequence to TCP-353 (SEQ ID NOS 25, 3, 28 and 3, respectively, in order of appearance), which were found on protein databases by the BLAST search. In the figure, | indicates that amino acids are matched, and : indicates that amino acids are similar.

SEQUENCE LISTING

<160> NUMBER OF SEQ ID NOS: 30

Figure 1:
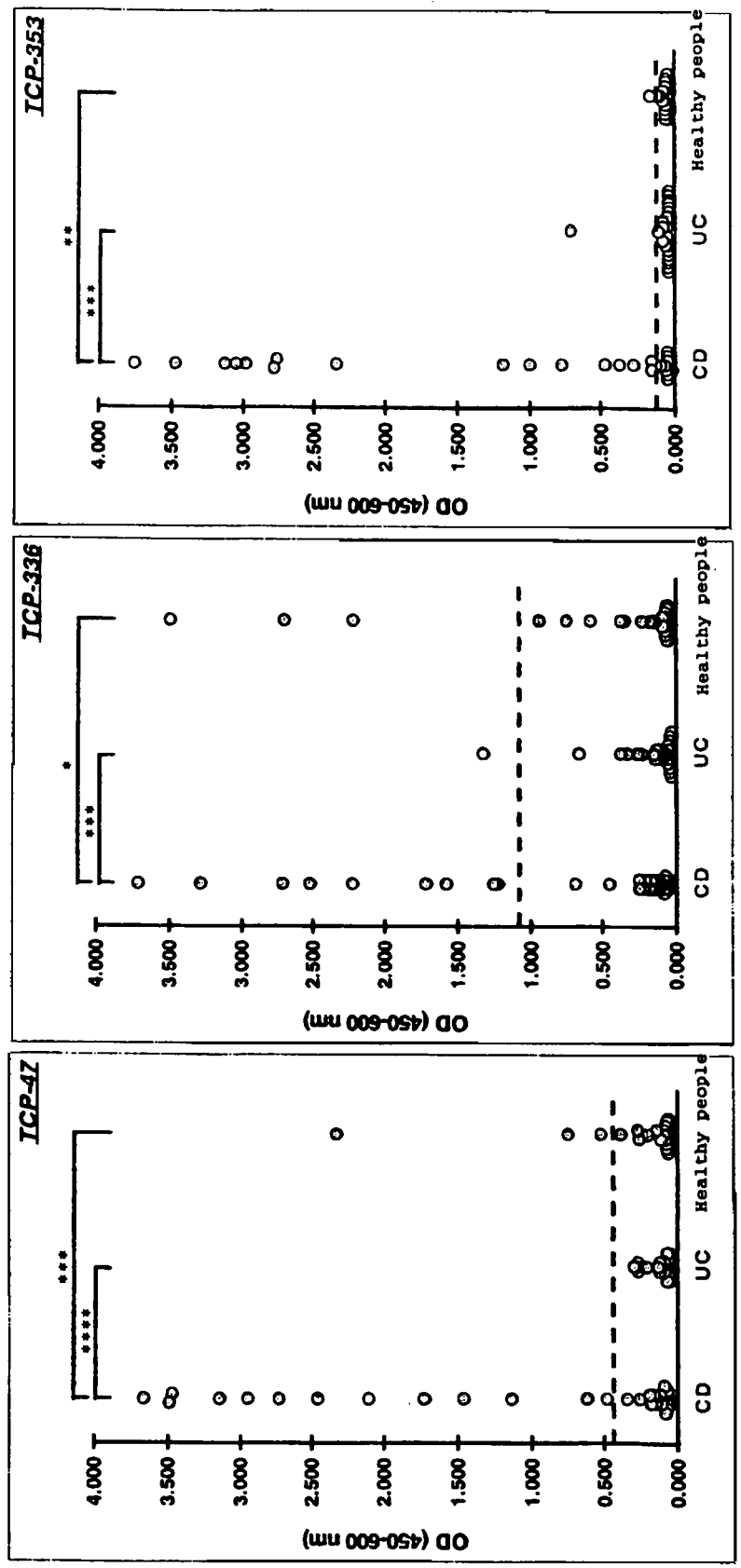
FIG. 1 is scatter diagrams which show the results of measurement by ELISA of the reactivity of the Crohn's disease antibody epitope peptides (TCP-47, TCP-336, and TCP-353) obtained in Example 1 with Crohn's disease patient sera (abbreviated as CD) (32 samples), ulcerative colitis patient sera (abbreviated as UC) (32 samples), and healthy people sera (32 samples). In the figure, *, , *, and **** indicate statistical significance levels, when the reactivity of each of the peptides with the Crohn's disease patient sera was compared with that with the ulcerative colitis patient sera or that with the healthy people sera (*: $p<0.05$, : $p<0.01$, *: $p<0.001$, and ****: $p<0.0001$; by the Mann-Whitney U test). Further, the dotted lines indicate the cut-off values.
Figure 2:
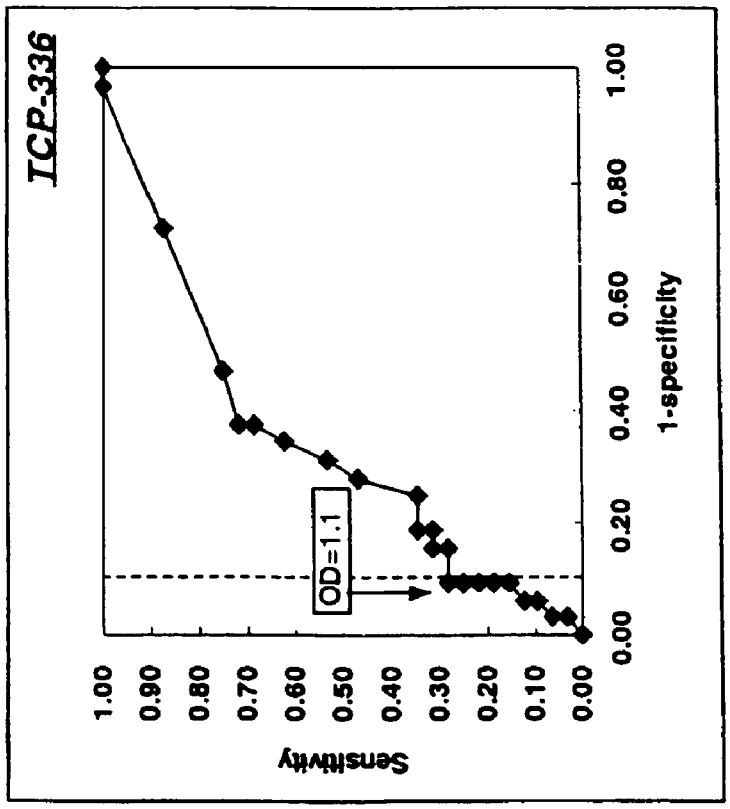
FIG. 2 shows ROC curves obtained by ELISA with TCP-47 or TCP-336, wherein sensitivity and 1-specificity were obtained and plotted along the vertical and horizontal axes, respectively, based on the measured values by ELISA of the 32 samples of the Crohn's disease patient sera and the 32 samples of the healthy people sera. In the figure, the dotted lines indicate the cut-off values.
Figure 2:
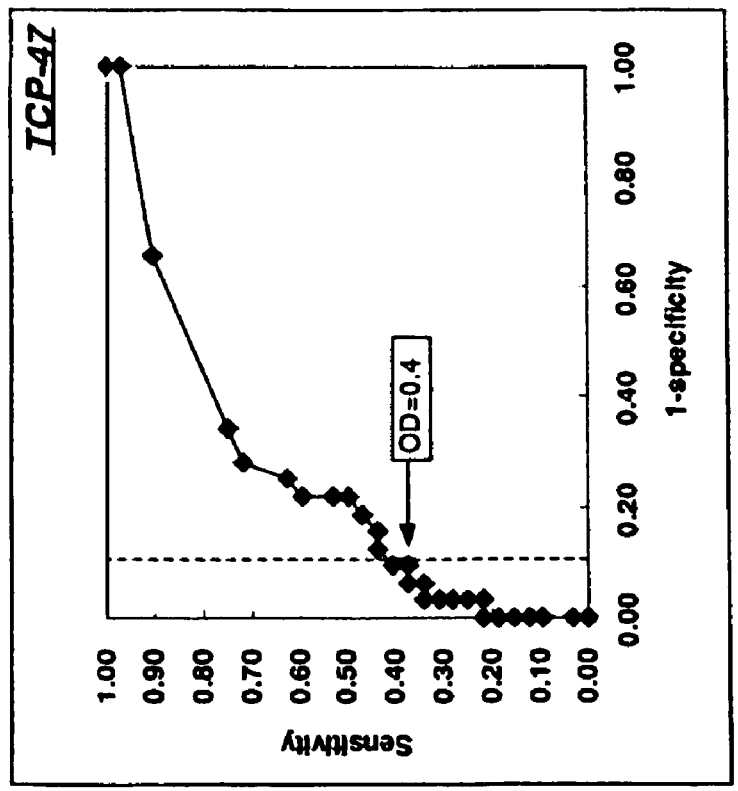
Figure 3:
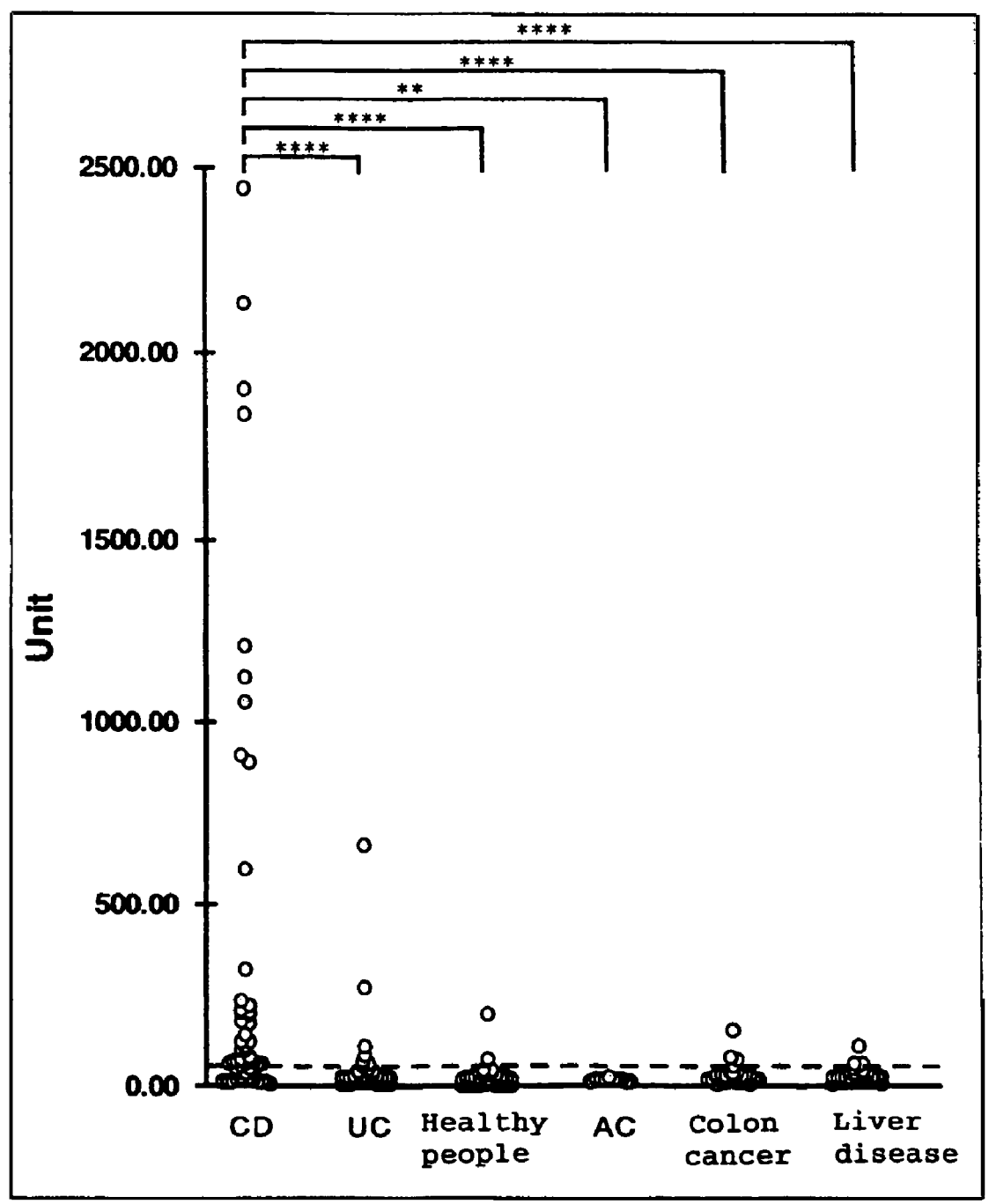
FIG. 3 is a scatter diagram which shows the results of measurement by ELISA of the reactivity of TCP-353 with Crohn's disease patient sera (CD, 60 samples), ulcerative colitis patient sera (UC, 109 samples), acute enteritis patient sera (11 samples), colon cancer patient sera (35 samples), chronic liver disease patient sera (49 samples), and healthy people sera (71 samples). In the figure,  and  indicate statistical significance levels, when the reactivity of TCP-353 with the Crohn's disease patient sera was compared with that with various patient sera and that with the healthy people sera (: $p<0.01$, and ****: $p<0.0001$; by the Mann-Whitney U test). Further, the dotted line indicates the cut-off value.
Figure 4:
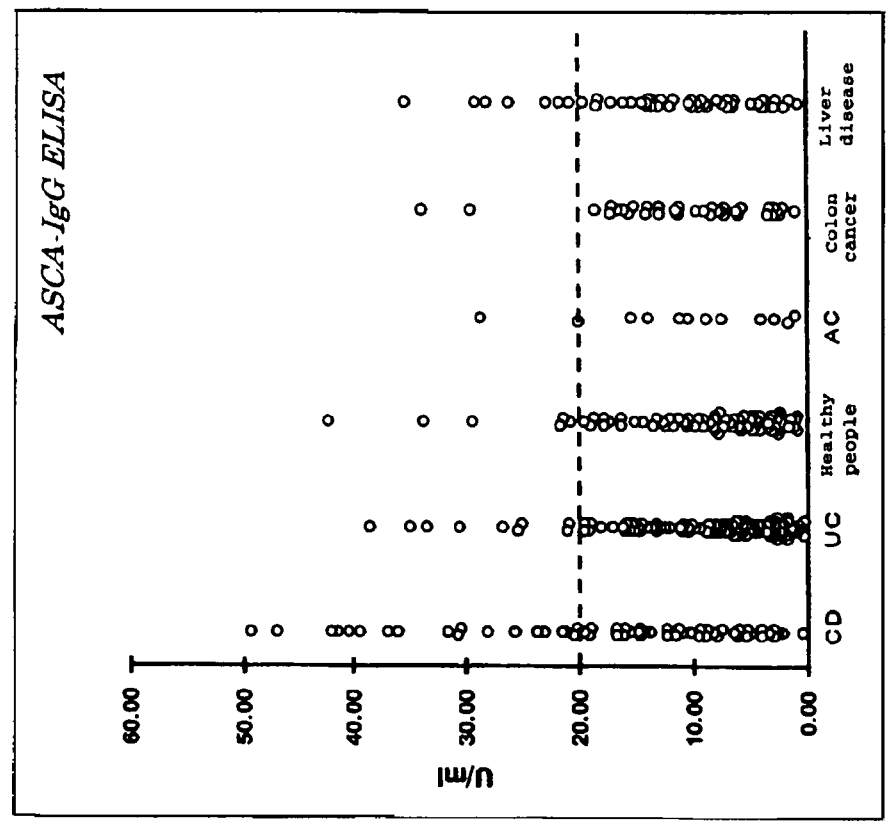
FIG. 4 shows the results by comparison between ASCA-IgG ELISA and TCP-353 ELISA, which is scatter diagrams showing the results of measurement by ELISA of the reactivity with Crohn's disease patient sera (CD, 60 samples), ulcerative colitis patient sera (UC, 109 samples), acute enteritis patient sera (11 samples), colon cancer patient sera (35 samples), chronic liver disease patient sera (49 samples), and healthy people sera (71 samples). Further, the dotted lines indicate the cut-off values.
Figure 4:
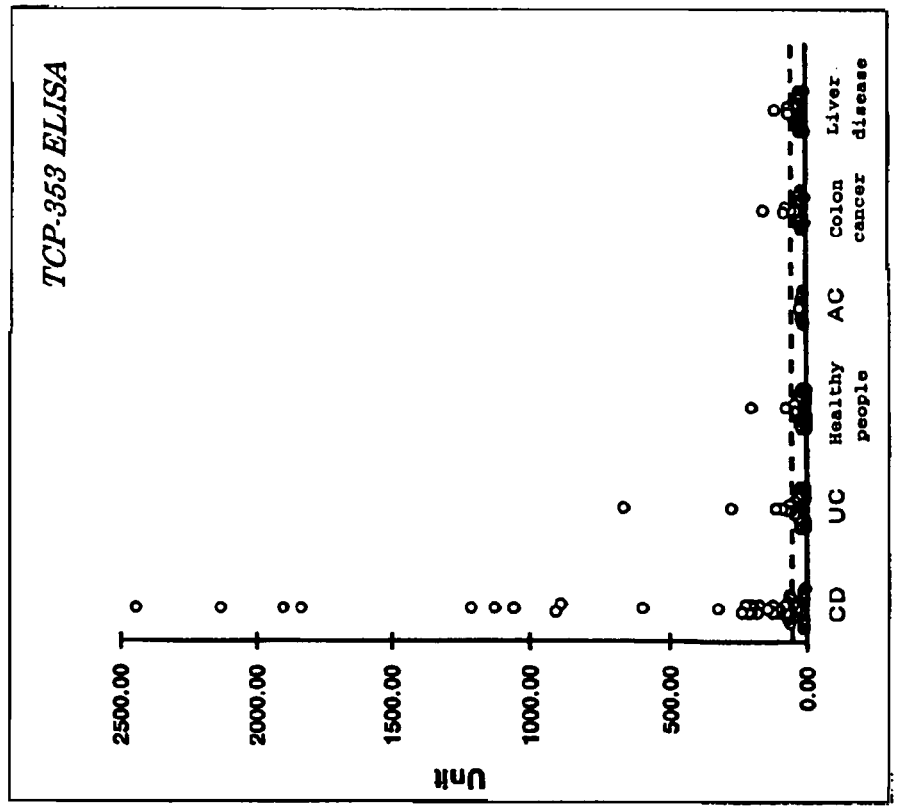
Figure 5:
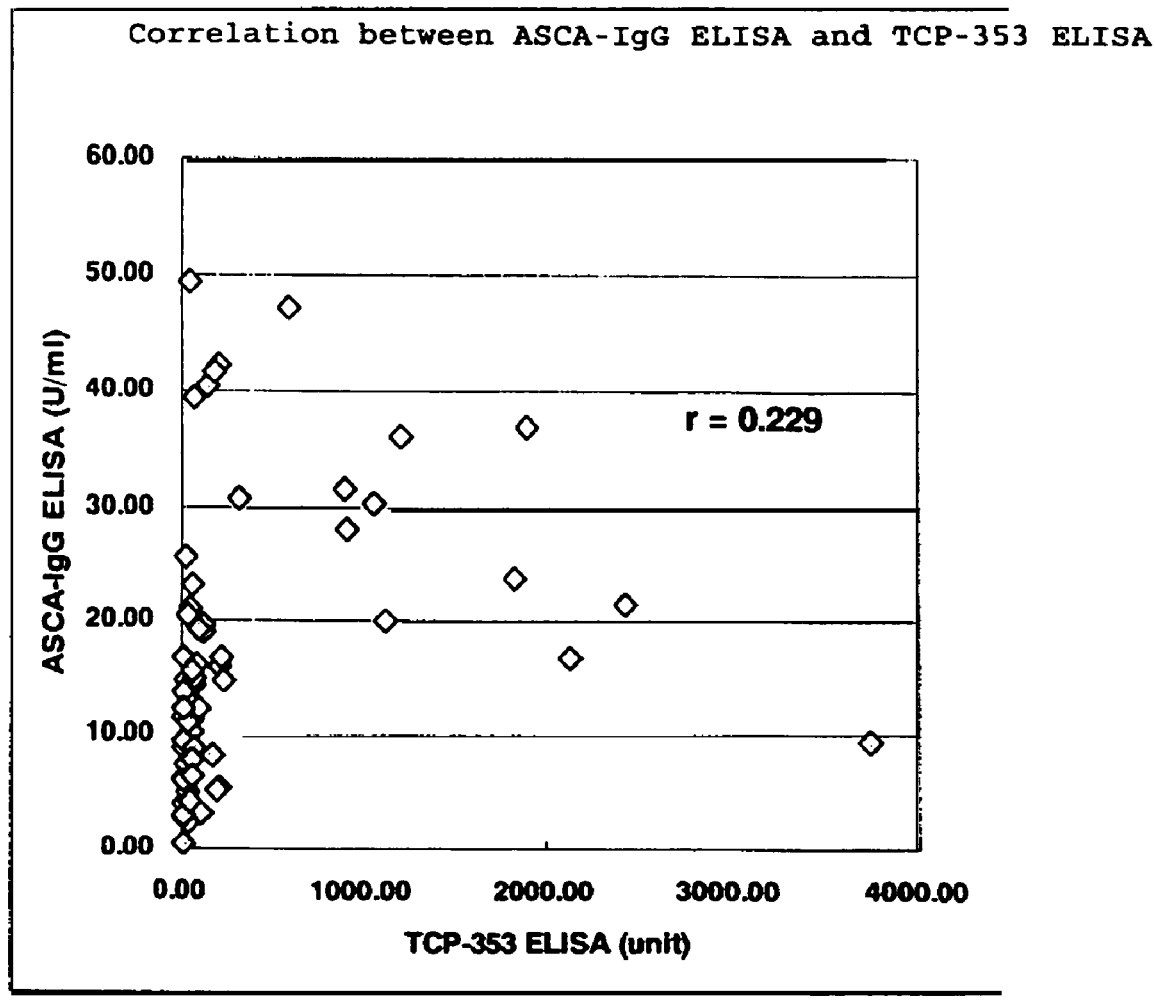
FIG. 5 shows the correlation between TCP-353 ELISA and ASCA-IgG ELISA. The measured values of the Crohn's disease patient sera by ASCA-IgG ELISA and by TCP-353 ELISA are plotted along the vertical and horizontal axes, respectively. The letter r is a correlation coefficient.
Figure 6:
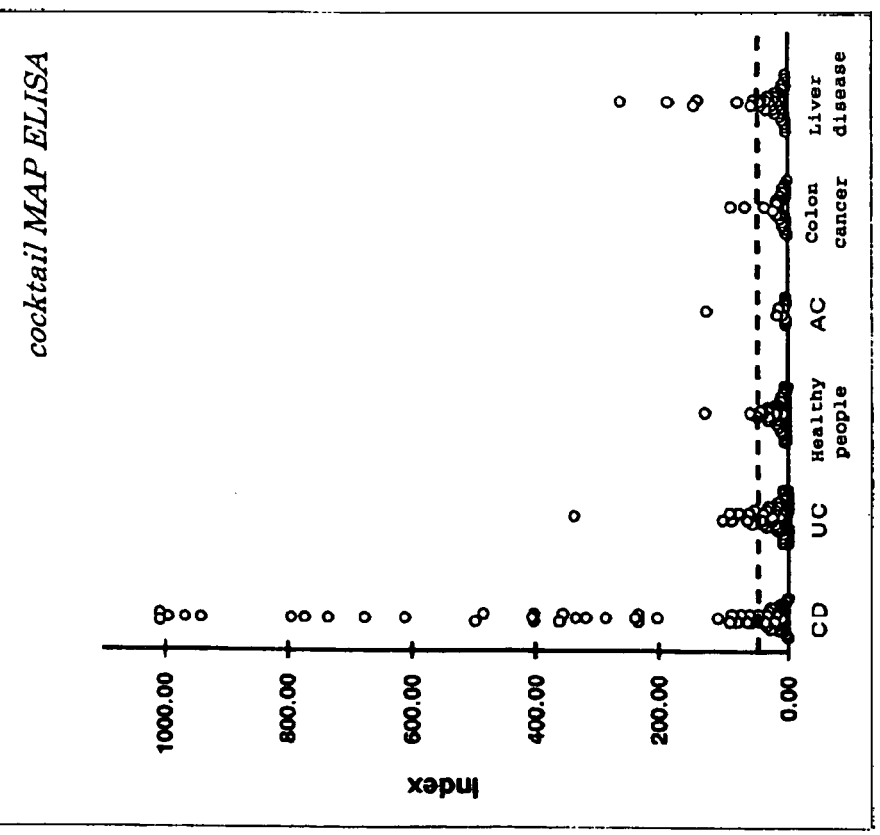
FIG. 6 shows the results by comparison between TCP-353 ELISA and cocktail-MAP ELISA, which is scatter diagrams showing the results of measurement by ELISA of the reactivity with Crohn's disease patient sera (CD, 60 samples), ulcerative colitis patient sera (UC, 109 samples), acute enteritis patient sera (11 samples), colon cancer patient sera (35 samples), and chronic liver disease patient sera (49 samples), and healthy people sera (71 samples). Further, the dotted lines indicate the cut-off values.
Figure 6:
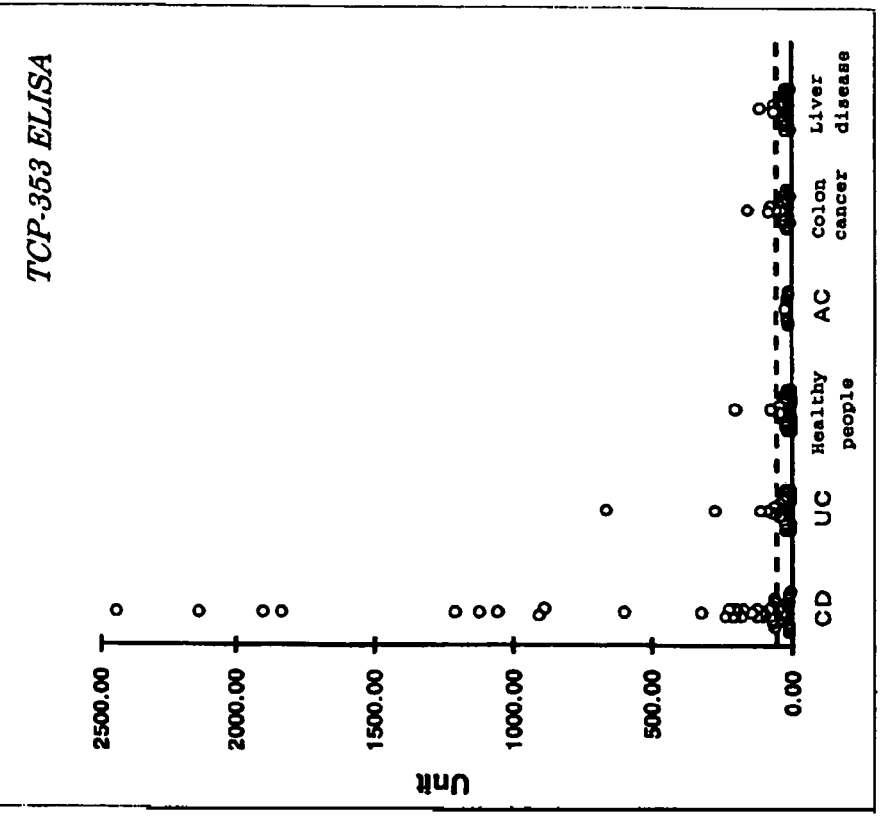
Figure 7:
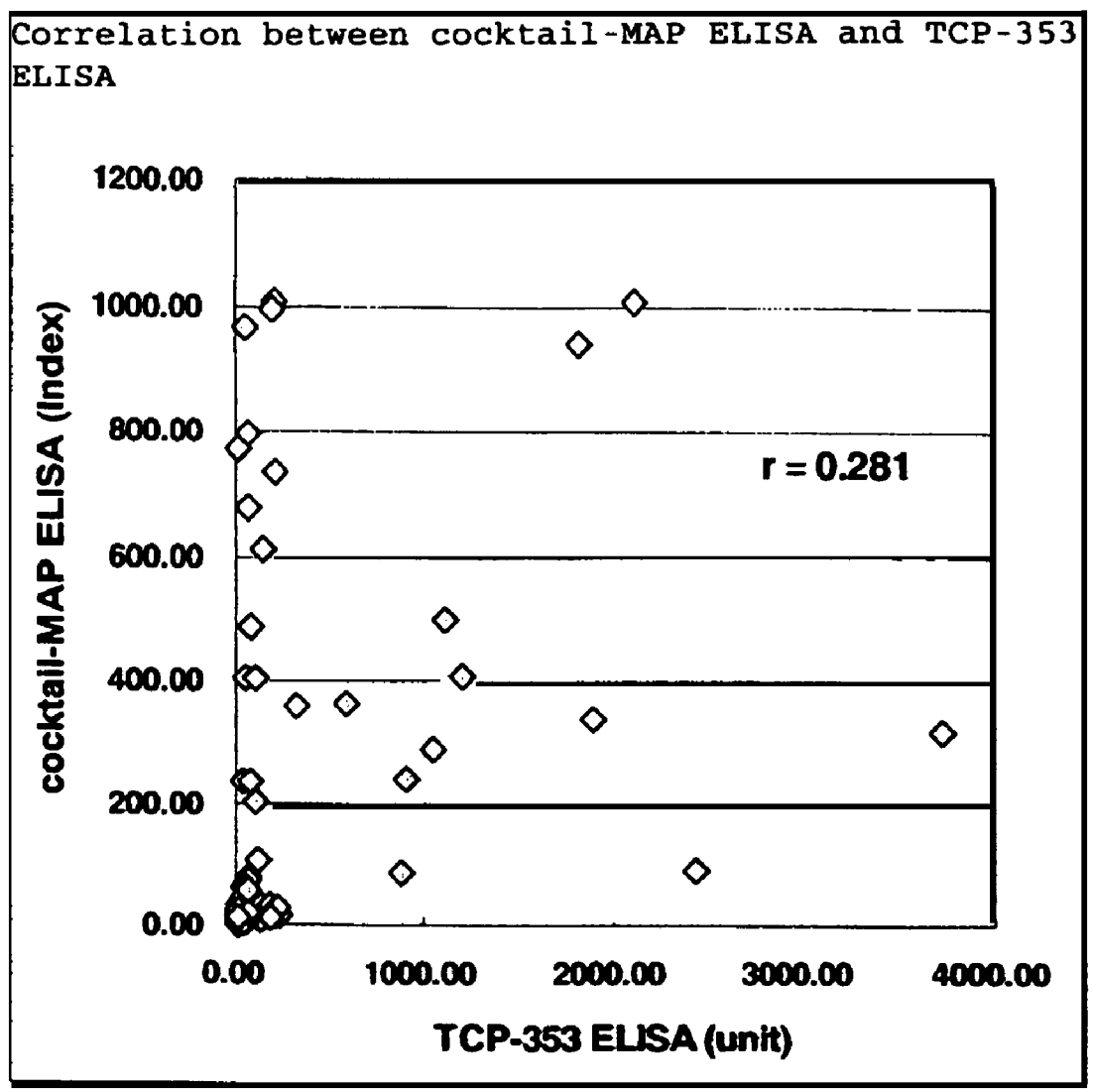
FIG. 7 shows the correlation between cocktail-MAP ELISA and TCP-353 ELISA. The measured values of the Crohn's disease patient sera by cocktail-MAP ELISA and by TCP-353 ELISA are plotted along the vertical and horizontal axes, respectively. The letter r is a correlation coefficient.

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Asn Ser Val Lys Asn Glu Val Glu Glu Val Thr Phe Thr Lys His Thr
1               5                   10                  15

Gln Cys Leu Gly Cys Phe Lys Ser Gly Phe Ser
            20                  25

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ile Pro Ala Leu Ser Glu Ala Glu Ala Gly Gly Ser Pro Glu Val
1               5                   10                  15

Arg Ser Ser Arg Pro Ala Trp Pro Ile Trp
            20                  25

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Ile Arg Gly Leu Phe Pro Asn
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Val Glu Glu Val Thr Phe Thr Lys
1               5

<210> SEQ ID NO 5
<211> LENGTH: 9
<212> TYPE: PRT
<213> ORGANISM: Drosophila melanogaster

<400> SEQUENCE: 5

Glu Val Asp Glu Val Thr Phe Thr Lys
1               5

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Glu Glu Val Thr Phe Thr Lys His Thr Gln Cys Leu Gly Cys Phe
1               5                   10                  15

-continued

Lys Ser Gly Phe
        20

<210> SEQ ID NO 7
<211> LENGTH: 16
<212> TYPE: PRT
<213> ORGANISM: Neurospora crassa

<400> SEQUENCE: 7

Val Glu Arg Lys Arg Glu Val Thr Leu Gly Cys Phe Lys Ser Asp Phe
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Val Glu Glu Val Thr Phe Thr Lys His Thr
1               5                   10

<210> SEQ ID NO 9
<211> LENGTH: 11
<212> TYPE: PRT
<213> ORGANISM: Encephalomyocarditis virus

<400> SEQUENCE: 9

Asp Val Asp Glu Val Ala Phe Ser Lys His Thr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Ser Val Lys Asn Glu Val Glu Glu Val Thr
1               5                   10

<210> SEQ ID NO 11
<211> LENGTH: 11
<212> TYPE: PRT
<213> ORGANISM: Dictyosterium discoideum

<400> SEQUENCE: 11

Asn Ser Val Lys Asn Asp Val Asp Glu Ser Thr
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Ser Val Lys Asn Glu Val Glu Glu Val Thr Phe Thr Lys His Thr
1               5                   10                  15

Gln

```
<210> SEQ ID NO 13
<211> LENGTH: 17
<212> TYPE: PRT
<213> ORGANISM: Trichodesmium erythraeum

<400> SEQUENCE: 13

Asp Asn Val Lys Ile Glu Val Glu Glu Val Ile Asn Lys His Ile Thr
1               5                   10                  15

Gln

<210> SEQ ID NO 14
<211> LENGTH: 13
<212> TYPE: PRT
<213> ORGANISM: Plasmodium falciparum

<400> SEQUENCE: 14

Asn Asn Val Lys Glu Glu Val Glu Glu Lys His Ser Glu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Glu Glu Val Thr Phe Thr Lys His Thr Gln Cys
1               5                   10

<210> SEQ ID NO 16
<211> LENGTH: 20
<212> TYPE: PRT
<213> ORGANISM: Plasmodium rubrum

<400> SEQUENCE: 16

Val Glu Cys Asp Val Thr Phe Thr Lys Asp Arg Gln Lys Val Cys Arg
1               5                   10                  15

His Ser Gln Cys
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Ser Val Lys Asn Glu Val Glu Glu Val Thr Phe Thr Lys His Thr
1               5                   10                  15

Gln Cys Leu Gly
            20

<210> SEQ ID NO 18
<211> LENGTH: 15
<212> TYPE: PRT
<213> ORGANISM: Pyrococcus horikoshii

<400> SEQUENCE: 18

Asn Ser Val Lys Asp Glu Val Lys Glu Phe Thr Asn Gln Leu Gly
1               5                   10                  15
```

```
<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Val Glu Glu Val Thr Phe
1               5

<210> SEQ ID NO 20
<211> LENGTH: 7
<212> TYPE: PRT
<213> ORGANISM: Homo sapiens

<400> SEQUENCE: 20

Glu Val Glu Glu Val Thr Phe
1               5

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Ile Pro Ala Leu Ser Glu Ala Glu Ala Gly Gly Ser Pro Glu Val
1               5                   10                  15

Arg Ser Ser Arg Pro Ala Trp Pro
            20

<210> SEQ ID NO 22
<211> LENGTH: 24
<212> TYPE: PRT
<213> ORGANISM: Homo sapiens

<400> SEQUENCE: 22

Val Ile Pro Ala Leu Trp Glu Ala Glu Val Gly Gly Ser Pro Glu Val
1               5                   10                  15

Arg Ser Ser Arg Pro Ala Trp Pro
            20

<210> SEQ ID NO 23
<211> LENGTH: 26
<212> TYPE: PRT
<213> ORGANISM: Homo sapiens

<400> SEQUENCE: 23

Val Ile Pro Ala Leu Trp Glu Ala Glu Ala Gly Glu Ser Pro Glu Val
1               5                   10                  15

Arg Ser Leu Arg Pro Ala Trp Pro Thr Trp
            20                  25

<210> SEQ ID NO 24
<211> LENGTH: 26
<212> TYPE: PRT
<213> ORGANISM: Homo sapiens

<400> SEQUENCE: 24

Val Ile Pro Ala Leu Trp Lys Ala Glu Ala Gly Gly Leu Pro Glu Leu
1               5                   10                  15
```

```
Arg Ser Ser Arg Pro Ala Trp Thr Thr Trp
            20                  25

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Arg Gly Leu Phe Pro Asn
1               5

<210> SEQ ID NO 26
<211> LENGTH: 7
<212> TYPE: PRT
<213> ORGANISM: Oryza sativa

<400> SEQUENCE: 26

Ile Arg Gly Leu Phe Pro Asn
1               5

<210> SEQ ID NO 27
<211> LENGTH: 12
<212> TYPE: PRT
<213> ORGANISM: Azotobacter vinelandii

<400> SEQUENCE: 27

Met Ile Arg Gly Leu Phe Phe Val Ile His Pro Asn
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Ile Arg Gly Leu Phe Pro
1               5

<210> SEQ ID NO 29
<211> LENGTH: 7
<212> TYPE: PRT
<213> ORGANISM: Caenorhabditis elegans

<400> SEQUENCE: 29

Leu Ile Arg Gly Leu Phe Pro
1               5

<210> SEQ ID NO 30
<211> LENGTH: 8
<212> TYPE: PRT
<213> ORGANISM: Leishmania major

<400> SEQUENCE: 30

Leu Ile Arg Ser Leu Phe Pro Asn
1               5
```

The invention claimed is:

1. An isolated peptide comprising an epitope to a Crohn's disease antibody, which is represented by the amino acid sequence as set forth in represented by SEQ ID NO:3, or a salt thereof.

2. A test reagent for Crohn's disease, comprising, as an active ingredient, the peptide defined in claim 1.

3. A test kit for Crohn's disease, comprising the test reagent defined in claim 2 as an antigen substance to a Crohn's disease antibody.

4. A test method for Crohn's disease, comprising a step of contacting the peptide defined in claim 1 with a biological specimen and detecting whether an antibody that binds to said peptide is present in the biological specimen.

* * * * *